(12) United States Patent
Mason

(10) Patent No.: US 11,603,245 B2
(45) Date of Patent: *Mar. 14, 2023

(54) SEXUAL ASSAULT EVIDENCE COLLECTION KIT USABLE BY A VICTIM

(71) Applicant: Secure Investigation Inc., Seaside Park, NJ (US)

(72) Inventor: Jane Mason, Seaside Park, NJ (US)

(73) Assignee: Secure Investigation Inc., Seaside Park, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/530,424

(22) Filed: Nov. 18, 2021

(65) Prior Publication Data

US 2022/0371803 A1 Nov. 24, 2022

Related U.S. Application Data

(63) Continuation of application No. 17/324,012, filed on May 18, 2021, now Pat. No. 11,186,418.

(51) Int. Cl.
*B65D 77/06* (2006.01)
*A61F 15/00* (2006.01)
(Continued)

(52) U.S. Cl.
CPC .............. *B65D 77/06* (2013.01); *A61B 42/10* (2016.02); *A61B 50/36* (2016.02); *A61F 15/001* (2013.01); *B65D 77/28* (2013.01); *G09B 19/003* (2013.01)

(58) Field of Classification Search
CPC ........ B65D 77/06; B65D 85/00; B65D 69/00; B65D 77/00; B65D 77/28; A61F 15/001;
(Continued)

(56) References Cited

U.S. PATENT DOCUMENTS 5,025,920 A * 6/1991 Walsh .................. B01L 1/52
206/456
D330,726 S 11/1992 Craven
(Continued)

OTHER PUBLICATIONS

Knight, Victoria, "A Dubious Product: A Rape Kit for Home Use," Kaiser Health News, Sep. 13, 2019, retrieved from https://khn.org/news/a-dubious-product-a-rape-kit-for-home-use/ (5 pages).
(Continued)

*Primary Examiner* — Rafael A Ortiz
(74) *Attorney, Agent, or Firm* — Arc IP Law, PC; Joseph J. Mayo

(57) ABSTRACT

A sexual assault evidence collection kit that may be used by the victim or other non-professionals. The kit may be simplified compared to kits for professional use, and may be usable with no specialized training. Victims may therefore be able to collect evidence themselves after an assault, instead of searching for a facility with personnel trained in forensic evidence collection, and enduring a long, intrusive examination. Embodiments may include a package (for example a clear bag) and the following components inside the package: gloves, swabs, swab containers, water, evidence collection bags, evidence bag sealing tape, evidence collection tape, a permanent marker, and instructions on how to identify, collect, seal, document, and store evidence.

6 Claims, 4 Drawing Sheets

(51) Int. Cl.
*A61B 50/36* (2016.01)
*B65D 77/28* (2006.01)
*A61B 42/10* (2016.01)
*G09B 19/00* (2006.01)

(58) Field of Classification Search
CPC ... A61F 17/00; A61B 42/10; A61B 2050/375; A61B 50/39; A61B 50/37; A61B 50/36; A61B 17/50
USPC .......................................... 206/223, 569–572
See application file for complete search history.

(56) References Cited

U.S. PATENT DOCUMENTS

| | | | |
|---|---|---|---|
| 5,718,245 A * | 2/1998 | Horn .................. | A61B 50/30 |
| | | | 128/897 |
| 5,979,658 A * | 11/1999 | Allen .................. | A61F 17/00 |
| | | | 206/229 |
| 6,171,260 B1 * | 1/2001 | Hochmeister ...... | A61B 10/0096 |
| | | | 600/572 |
| 10,634,584 B2 * | 4/2020 | Farris ................. | G01N 1/2813 |
| 10,968,644 B2 | 4/2021 | Apostolopoulos et al. | |
| 2007/0175774 A1 | 8/2007 | Smart et al. | |
| 2009/0291449 A1 * | 11/2009 | Knapp, Jr. ........... | B01L 3/545 |
| | | | 435/6.12 |
| 2011/0036746 A1 * | 2/2011 | Bear .................. | G09B 19/0084 |
| | | | 206/572 |
| 2017/0296284 A1 | 10/2017 | Turturro et al. | |
| 2018/0008361 A1 | 1/2018 | Lundstrom et al. | |
| 2019/0060030 A1 | 2/2019 | Haines | |
| 2021/0087371 A1 | 3/2021 | Kwon et al. | |
| 2022/0061431 A1 * | 3/2022 | Krueger ............. | A41D 19/0082 |

OTHER PUBLICATIONS

Wikipedia, "Rape Kit" retrieved from https://en.wikipedia.org/wiki/Rape_kit on Mar. 31, 2021 (14 pages).

Hanson, Melissa, "What is a rape kit and how is it collected? A close look at one of the most difficult tests you hope to never have to take," Advance Local; Updated Jan. 7, 2019, Posted Jul. 11, 2017 (8 pages).

* cited by examiner

SEXUAL ASSAULT EVIDENCE COLLECTION KIT USABLE BY A VICTIM

This patent application is a continuation of U.S. Utility patent application Ser. No. 17/324,012, filed 18 May 2021, issued as U.S. Pat. No. 11,186,418, the specifications of which are hereby incorporated herein by reference.

BACKGROUND OF THE INVENTION

Field of the Invention

One or more embodiments of the invention are related to the field of evidence collection. More particularly, but not by way of limitation, one or more embodiments of the invention enable a sexual assault evidence collection kit that may be used by a victim of the assault.

Description of the Related Art

Existing rape kits are kits sold by forensic supply companies to medical facilities and to law enforcement. They are designed to be used by specially trained professionals, typically in an institutional setting such as a hospital.

At least 77% of sexual assault victims do not go to the hospital for a rape kit. Many victims don't know how to react in the aftermath of the crime, which is the critical time period for evidence collection. Medical facilities won't do a rape kit on victims after the first three to five days postcrime.

Existing rape kits are often designed to collect evidence that is rarely, if ever, used by crime labs or prosecutors. For example, some kits require the collection of pubic hair exemplars (which is painful and traumatic) from the crime victim, while the related crime lab hasn't required them for years. Kits typically include giant sheets of paper that the crime victim stands naked on while her body is combed and examined. Any trace evidence collected on the sheet is then preserved as evidence. Crime lab technicians almost never analyze this trace evidence.

Existing rape kits require trained professionals that know how to use the kit to collect evidence. There is a dearth of sexual assault nurse examiners, which is a specialty created in the nursing profession. Nurses must take a special course, often at their own expense and on their own time, to become qualified. Few places offer this training.

As a result of the lack of qualified professionals, a victim is often told when they reach the hospital that there are no medical personnel trained to perform the kit. Victims may be sent to two or three different facilities before finding a person to do the rape kit. People in rural areas have a worse time finding a place to obtain a rape kit. For example, in Alaska victims must sometimes take a plane to get to a location that has a rape kit and the personnel trained to use the kit.

The rape kits often take up to 8 to 12 hours to complete, and victims often describe the experience as re-traumatizing. So after spending hours finding a place that can do a rape kit, the victim may then deal with this lengthy ordeal.

There is no rape kit that exists currently for individual victim use. With such a kit, the victim could collect evidence right away, but they could still preserve it if they decide to do so 5 or more days later (assuming the evidence is still available/exists). With a simplified kit for at home use, the victim could quickly collect the most important evidence, and avoid the trauma of locating a facility and being subjected to a long, invasive examination conducted by strangers. Crime reporting rates may therefore increase, evidence collection may be more common and useful, and prosecution and conviction rates may increase, providing a more effective deterrent to sexual assaults.

For at least the limitations described above there is a need for a sexual assault evidence collection kit usable by a victim.

BRIEF SUMMARY OF THE INVENTION

One or more embodiments described in the specification are related to a sexual assault evidence collection kit usable by a victim of the assault. Embodiments of the invention may enable the victim to collect essential evidence quickly and privately, in a manner that ensures that the evidence is uncontaminated, correctly stored and documented, and ultimately admissible in a criminal, civil, or administrative proceeding if the victim chooses to pursue any of these options.

One or more embodiments of the evidence collection kit may include one or more pairs of gloves, swabs and swab containers, one or more containers that contain water, evidence collection bags, evidence collection bag sealing tape, evidence collection tape, a permanent marker, and evidence collection instructions. The kit may be configured to be used by a person without training on performing sexual assault forensic exams.

In one or more embodiments, the kit may include a report form for reporting the sexual assault.

In one or more embodiments, the kit may include a package configured to contain all of the items of the kit. The package may be clear, and may include a tamper-evident seal.

In one or more embodiments, the swabs may include cotton.

In one or more embodiments, the swab containers may be air drying swab containers. Air drying swab containers may for example have an air channel (or multiple channels), to facilitate drying of wet swabs.

In one or more embodiments, the gloves may be sterile gloves; for example they may be sterile nitrile gloves.

In one or more embodiments, the water may be sterile water.

In one or more embodiments, the evidence collection instructions may include: instructions on ensuring personal safety, instructions on photographing evidence, instruction on types of evidence to consider collecting, instructions on how to collect each type of evidence, instructions on how to package and seal collected evidence, instructions on how to label collected evidence, instructions on how to store collected evidence, and instructions on how to document the sexual assault.

In one or more embodiments, the kit may not contain for example any or all of: a sheet on which the victim stands, sits, or lies to catch evidence from the victim's body; a blood collection device; a urine collection container; a comb; tweezers; a nail pick; a glass slide.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A sexual assault evidence collection kit usable by a victim will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1B:
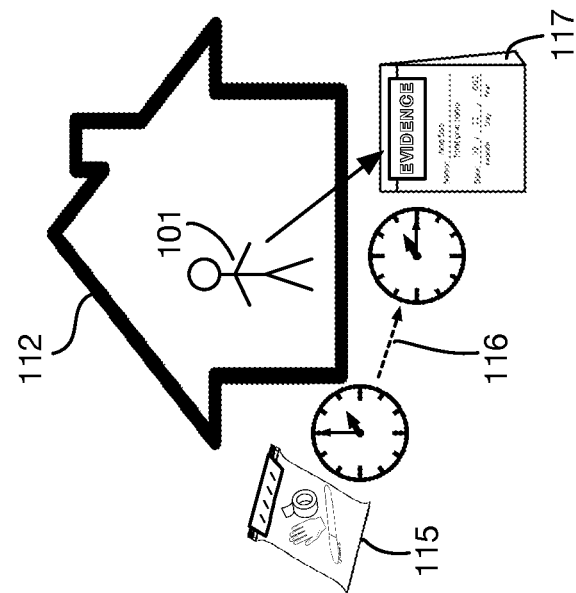
FIG. 1B shows a process of collecting evidence easily at home that is enabled by the invention.
Figure 1A:
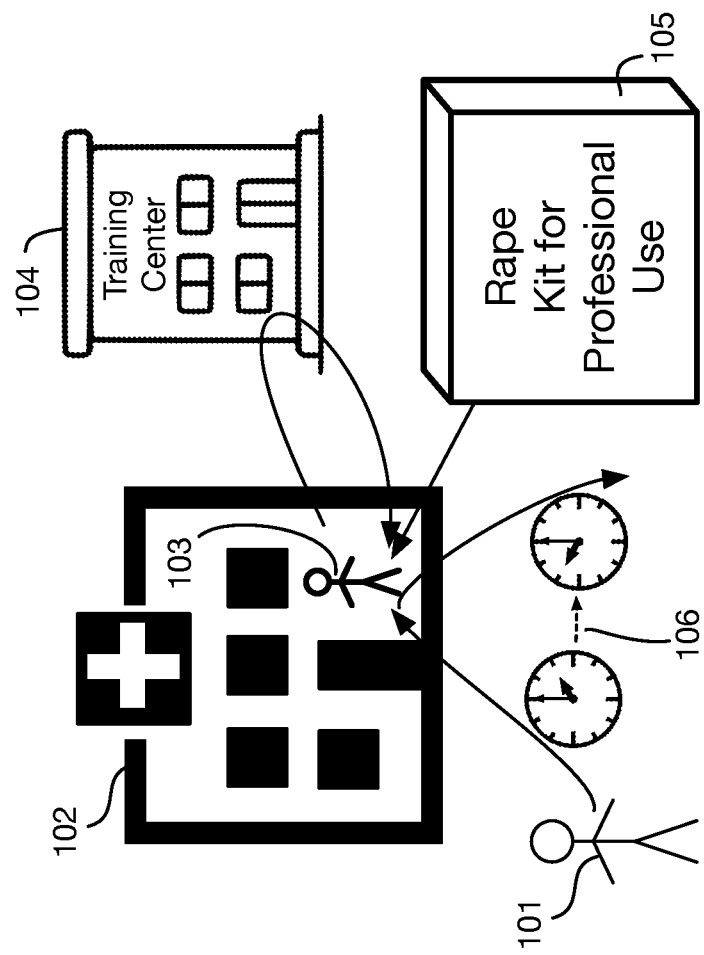
FIG. 1A shows a typical process used in the prior art to collect evidence from a sexual assault victim; this process is often intrusive, time-consuming, and difficult.

FIG. 1A shows a process that may be followed using existing sexual assault kits known in the art. These kits 105 are configured to be used by trained professionals, such as a nurse 103 who has received specialized training in forensic evidence collection for sexual assaults. This training may be time-consuming and not widely available; the nurse 103 may have to travel for example to another facility 104 to receive the training, which requires both a classroom component (in-person or online) and a clinical component. As a result, many medical facilities may not have staff trained to collect the evidence. There is also a very high burn-out rate for sexual assault nurses because of the trauma they see and the time demands of the job; this further contributes to shortages of qualified personnel who are trained to collect this evidence.

A victim 101 of a sexual assault must typically go to a facility 102, such as a hospital, to have the nurse 103 (or similar specially trained professional) collect evidence using the professional kit 105, if such a nurse is available. This process is intrusive and may be very time-consuming; the victim may need to spend many hours 106 at the facility, compounding the trauma of the initial assault.

FIG. 1B shows an evidence collection process that is enabled by embodiments of the invention. The victim 101 may obtain a simpler evidence collection kit 115, for example from a victim support service or in the mail. This kit 115 may be configured to be used directly by the victim 101 without any specialized training, unlike the professional kits 105 known in the art. The kit 115 may be used at home 112, instead of at a facility such as hospital 102. The kit 115 may be simplified and streamlined compared to the professional kit 105, containing only items that can be used by the victim to collect essential evidence. The time 116 that elapses between when the victim receives or starts using the kit 115 to when the complete evidence 117 is collected, sealed, and labeled, may be as little as 10 or 15 minutes, compared to the several hours 106 often required for the professional kit.

Figure 2:
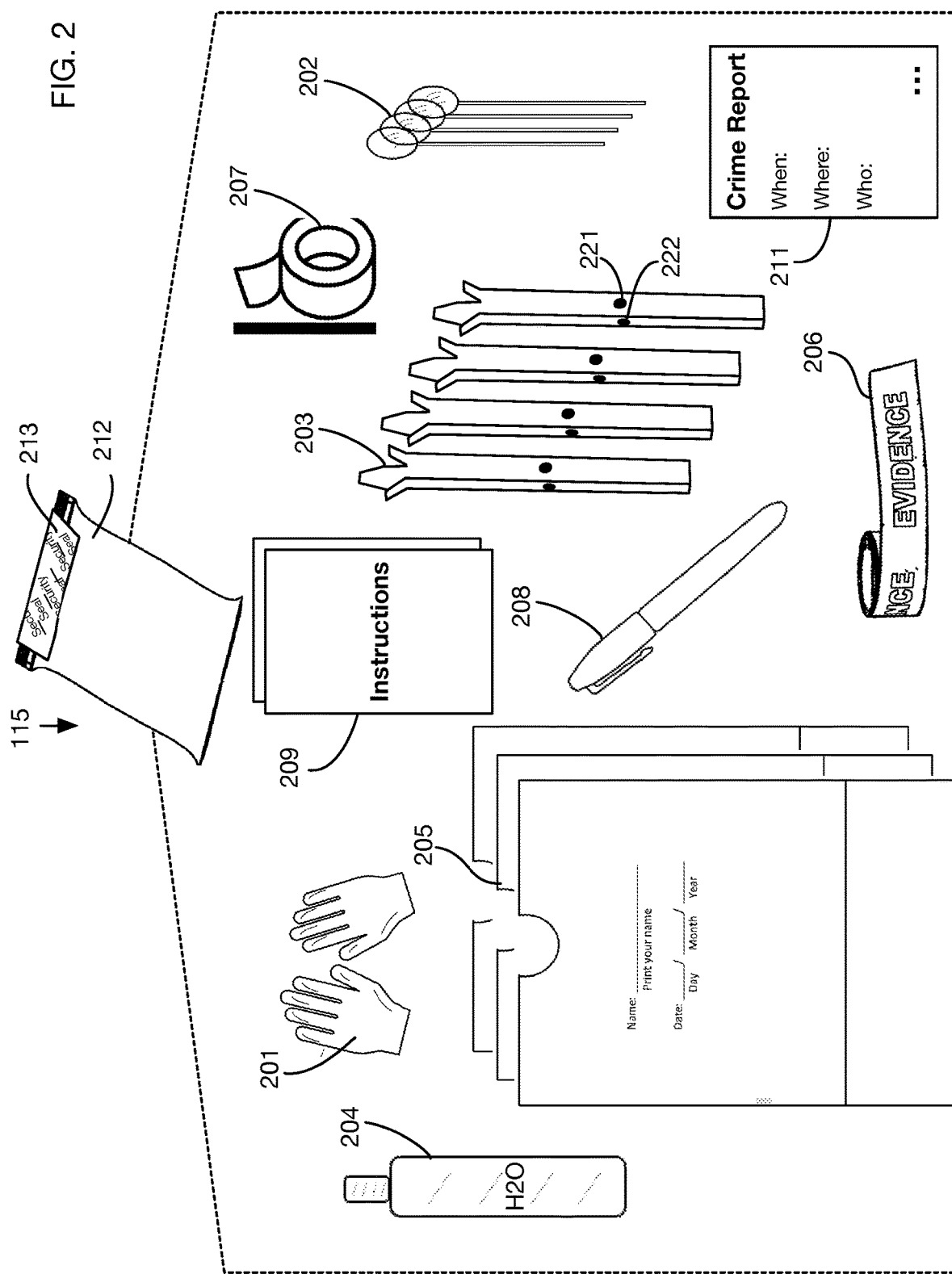
FIG. 2 shows contents of an illustrative embodiment of the invention.

FIG. 2 shows illustrative components of an embodiment of sexual assault evidence collection kit 115 that is configured to be used by the victim (or another person assisting the victim). The package 212 containing other items of kit 115 may be compact enough to be easily carried in a pocket, pocketbook, glove compartment of a car, or desk drawer. For example, an illustrative embodiment of the kit package 212 may be approximately six inches long and may be rolled into the shape of a scroll having an approximate two-inch diameter. The kit package 212 may for example be a clear bag which is sealed with a tamper resistant seal 213. An illustrative tamper resistant seal may be approximately 0.5 inch by 1.5 inch and will tear down the middle if tampered with. In another embodiment, the kit package 212 may include a clear bag which is heat sealed. This allows others to know if the kit has already been opened. Use of these seals is not meant to be limiting and any appropriate tamper resistant seal may be used on the external kit packaging.

Illustrative contents of the kit (in addition to the package) may include the following:

One or more pairs of gloves 201. One or more embodiments of the kit may contain at least two pairs of gloves, so that both the victim and someone helping the victim can collect evidence without contamination. In one or more embodiments, the gloves may for example be sterile gloves, such as sterile nitrile gloves. One or more embodiments may contain any type or types of gloves, in any quantity.

One or more swabs 202. One or more embodiments may contain multiple swabs so that evidence can be collected from multiple places. Swabs may have tips that are for example cotton, although other types of materials may be used instead of or in addition to cotton.

One or more swab containers 203. The swabs 202 may be placed into these containers after collection of evidence. In one or more embodiments, the swab containers 203 may be for example air drying swab containers. Wet items such as swabs generally need to be air dried. Trained professionals know how to air dry a swab without causing contamination. Once dry, they will package each swab in a separate swab container, such as a box or envelope. Air-drying a wet swab can be challenging for a novice. Air drying swab containers are designed so a wet swab can be stored inside it and the swab dries in place; this may simplify the collection process for the non-professional user. Air drying swab containers may for example have air channels such as illustrative holes 221 and 222 that allow air to pass through the swab container. One or more embodiments may contain any type or types of swab containers 203, including for example simple containers that may require pre-drying of swabs before they are placed into the containers, air drying swab containers, or containers that may dry swabs using any drying procedure or structure, including but not limited to use of air channels.

Water 204. This water may be provided in one or more containers. In one or more embodiments, the water 204 may be sterile. The degree to which the water is sterilized or purified may vary in one or more embodiments; for example, in some embodiments the water may be purified to be free (or essentially free) of nucleotides and nucleases. For collection of dried secretions, for example, the victim may place a drop of water 204 onto the tip of a swab 202 to collect the secretion.

One or more evidence collection bags 205, into which evidence may be placed for storage after it is collected. Bags may be any type of container of any size or shape.

Evidence collection bag sealing tape 206, which may be used for sealing the one or more evidence collection bags 205 securely after evidence is placed in the bags. The sealing tape may be packaged for example, without limitation, as a roll of tape, or with any type of tape dispenser, or it may be packaged as one or more strips of sealing tape. In one or more embodiments the sealing tape may be labeled, for example with "Evidence" or "Secure Seal" or some similar phrase. In one or more embodiments the sealing tape may be tamper-proof or tamper-evident.

Evidence collection tape 207. Professional kits often include combs or sheets that the victim stands on to collect evidence. Tape provides the same functionality and is simpler to use. The user only needs to daub the sticky side of the tape onto the evidence to collect it. Evidence collection tape 207 may be packaged for example, without limitation, as a roll of tape, or with any type of tape dispenser, or it may be packaged as one or more strips of evidence collection tape.

In one or more embodiments, the same type of tape may be used for evidence collection tape 207 and evidence collection bag sealing tape 206. For example, if a common type of tape is used, the kit may contain a single roll (or other package) of this tape that may be used for both evidence collection and evidence sealing.

One or more permanent markers 208 for labeling evidence containers.

Instructions 209 that instruct the user how to collect, seal, and store the evidence.

A report form 211 that may be used to report the assault, for example to the police or other authorities.

In one or more embodiments of the invention, kit 115 may not contain some of the items that are typically included in professional kits. The inventor has found that many of these items may be unnecessary for collection of basic evidence, and they may not be appropriate for use by the victim or another non-professional. For example, kit 115 may not contain any sheet (for example of paper) that a victim stands, sits, or lies on; these sheets are often used in professional kits to catch evidence that falls from the victim's body. Having the victim use such a sheet is impractical for home collection, and it adds little if any value to the evidence. Kit 115 may not contain a blood collection device (such as a needle) or a urine collection container. It may not contain certain specialized tools for evidence collection, such as a comb, tweezers, or a nail pick. It may not contain glass slides.

Figure 3:
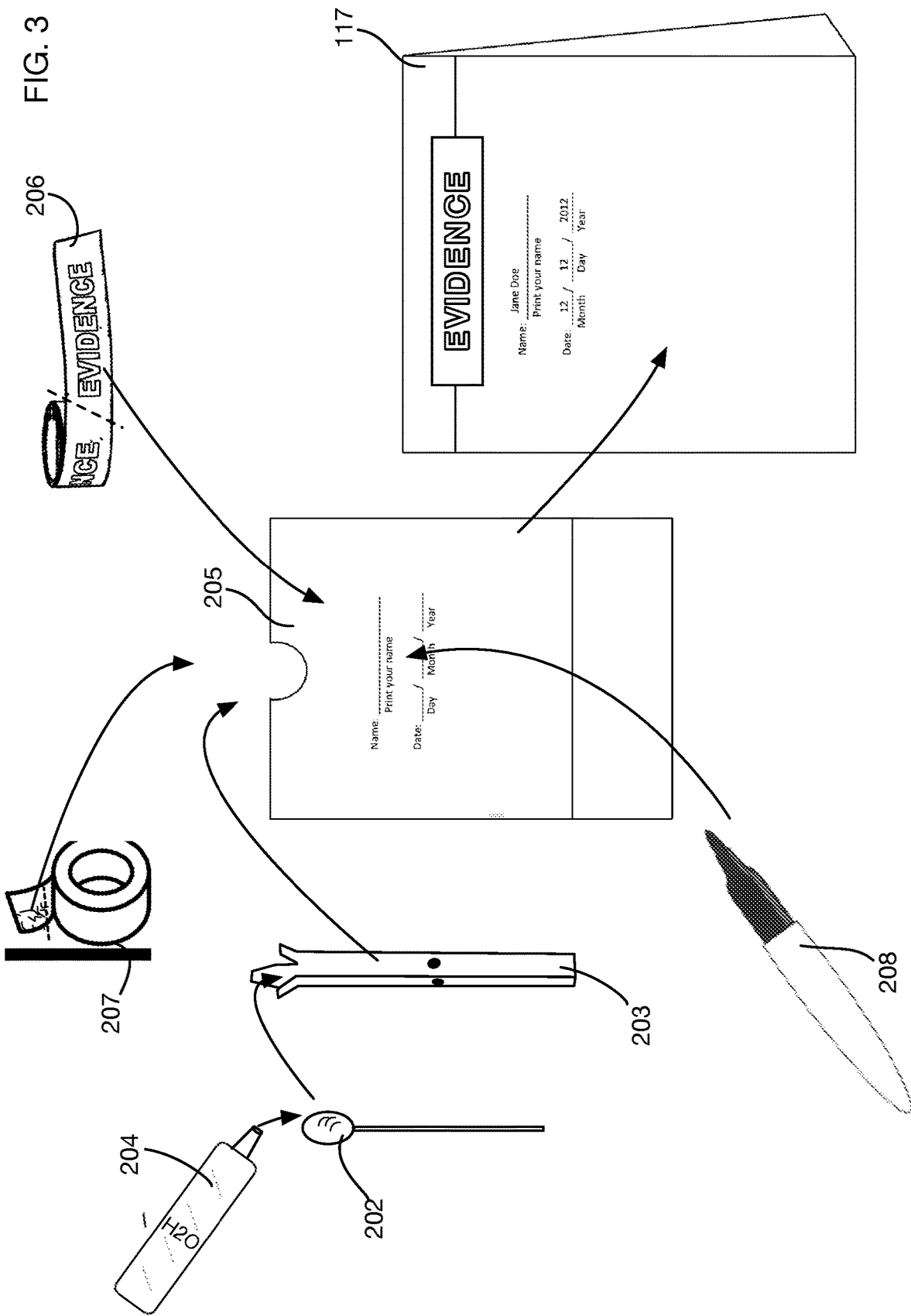
FIG. 3 shows illustrative steps in collecting, packaging, sealing, and labeling evidence using an embodiment of the invention.

FIG. 3 shows illustrative steps of evidence collection, sealing, labeling, and storing that may be performed using embodiment 115 of the invention. The user may for example take a swab 202, wet the tip with water 204, collect evidence with the wet tip, place the swab into air drying swab container 203, and close the swab container. Trace evidence may be collected with a piece of tape 207. The swab container 203 and piece of tape 207 may be placed into evidence collection bag 205, which may be folded and sealed with evidence collection bag sealing tape 206. The user may use marker 208 to label the bag 205. The filled, sealed, and labeled bag 117 may then be stored or submitted as evidence.

Figure 4:
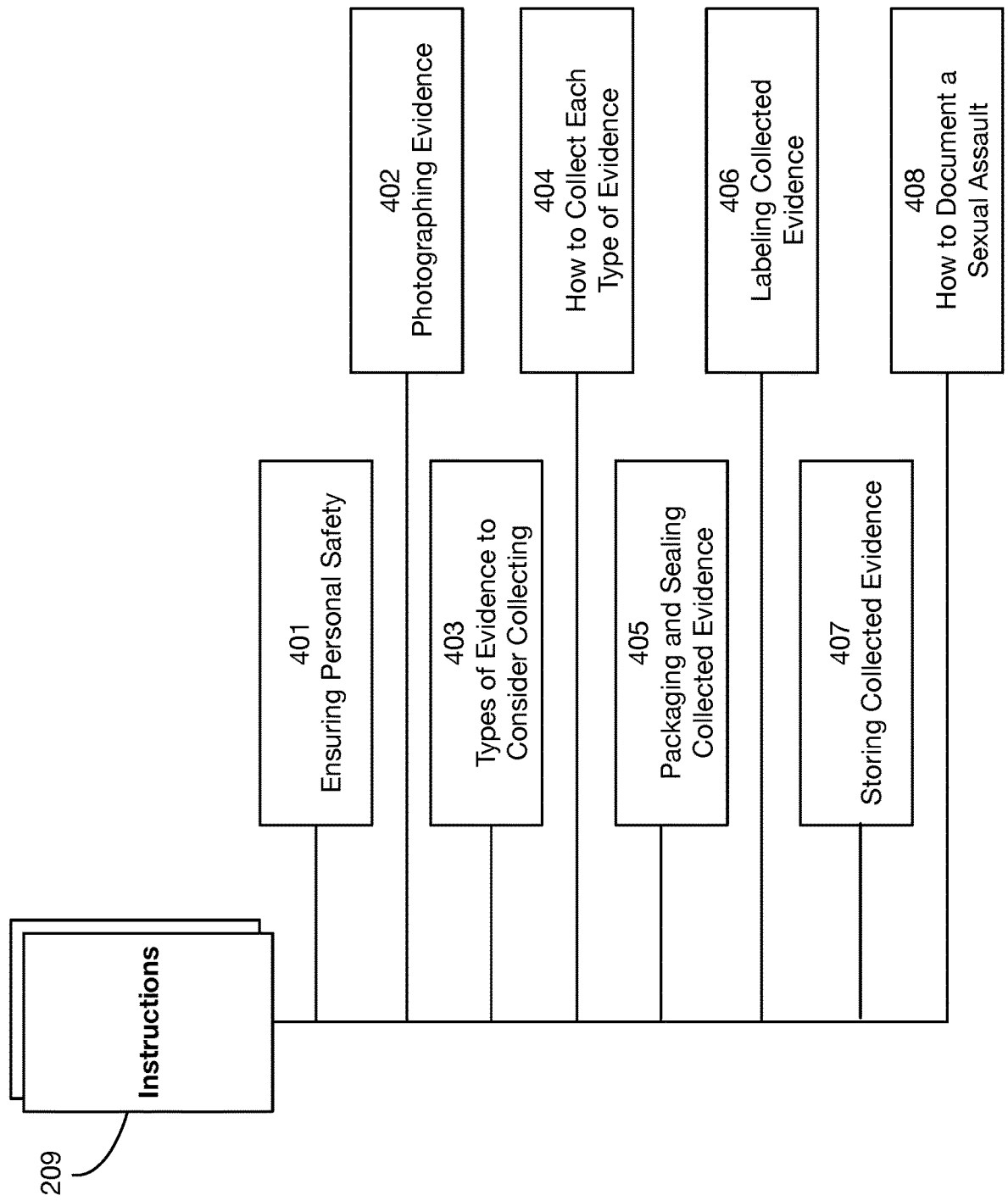
FIG. 4 shows illustrative contents of instructions that may be included in one or more embodiments of the invention.

FIG. 4 shows illustrative content that may be included in instructions 209 of the kit 115. Each instruction may include text, graphics, or both. For example, the instructions related to swabbing a dried secretion with suspected DNA may include one textual instruction element and one graphical instruction elements. The textual and graphical instruction elements may be positioned on the instructions by any suitable means. For example, they may be printed on the instruction sheet in conjunction with Spanish translation and disclaimers. Alternatively, for example, they may be printed on individual sheets whereby any translations, disclaimers, and other information may be on separate sheets of paper and included in the kit by any other suitable means.

The illustrative content shown in FIG. 4 may be presented in the instructions 209 in any order and with any organization; the sections of the instructions document need not match the content categories illustrated. One or more embodiments may include additional content, or may include only subsets of the content shown in FIG. 4.

Content 401 may describe steps for the victim to ensure their personal safety. For example, the victim may be advised to evaluate whether they require any help with issues like STDs, pregnancy, drug testing, medical assistance, and trauma assistance. They may be advised to consider going to a medical facility or to contact RAINN (Rape Abuse Incest National Network) or another hotline.

Content 402 may provide advice on photographing evidence. It may advise the victim to take as many photographs as possible so the crime scene can be reconstructed with photographic corroboration at a later time, presuming that the scene is in an accessible and safe location. It may suggest taking photos of any parts of the body with bruising, marks, stains, blood, bite marks, etc. Some bruising will not be visible immediately so additional photographs may need to be taken two to three days later.

Content 403 may describe the types of evidence that may be collected. Evidence is anything that will corroborate allegations. Some examples are the victim's injuries, the clothing the victim was wearing at the time of the assault, debris under the fingernails, the bedsheets, any type of semen, sweat, blood, saliva, or any other bodily fluid that is on the body or on any item, a glass with fingerprints, and any constraints used during the assault.

Content 404 may describe steps to collect each type of evidence, if applicable. This content may advise the order in which evidence should be collected, based for example on how quickly evidence may deteriorate. It may provide detailed instructions to collect items such as semen, sweat, blood, saliva, hairs and fibers, skin cells, dried secretions, fingerprints and other trace evidence from various locations including areas of the body.

Content 405 may describe steps to package and seal the evidence, so that it is preserved and so that there are no questions about the authenticity of the evidence.

Content 406 may describe steps to label the collected evidence with information such as the victim's name, the date, a description of the item, and where it was found.

Content 407 may provide information on how to store collected evidence so that it is not degraded by sunlight or heat.

Content 408 may describe how to prepare documentation of the sexual assault, and may advise documenting items such as any information of the perpetrator, the incident, the context and background, potential witnesses, and potential other sources of information or evidence.

While the invention herein disclosed has been described by means of specific embodiments and applications thereof, numerous modifications and variations could be made thereto by those skilled in the art without departing from the scope of the invention set forth in the claims.

What is claimed is:

1. A sexual assault evidence collection kit usable by a victim, comprising:
    a package configured to contain all items of said sexual assault evidence collection kit, wherein said package comprises a tamper-evident seal;
    one or more pairs of sterile gloves;
    a plurality of cotton swabs;

a plurality of air drying swab containers, wherein each swab container of said plurality of air drying swab containers comprises an air channel;
one or more containers that contain water;
a plurality of evidence collection bags;
evidence collection tape;
a permanent marker;
evidence collection instructions comprising
   instructions on photographing evidence;
   instruction on types of evidence to consider collecting;
   instructions on how to collect each type of evidence;
   instructions on how to package and seal collected evidence;
   instructions on how to label collected evidence;
   instructions on how to store collected evidence; and
   instructions on how to document a sexual assault; and,
a report form for reporting said sexual assault;
wherein
   said sexual assault evidence collection kit is configured to be used by a person without training on performing sexual assault forensic exams; and,
   said sexual assault evidence collection kit does not comprise any of
      a sheet on which a victim stands, sits, or lies to catch evidence from a victim's body;
      a blood collection device;
      a urine collection container;
      a glass slide.

2. The sexual assault evidence collection kit of claim 1, wherein said package is configured to be rolled into a shape of a scroll, wherein a diameter of said scroll is approximately two inches.

3. The sexual assault evidence collection kit of claim 1, wherein said one or more pairs of sterile gloves comprise two or more pair of sterile nitrile gloves.

4. The sexual assault evidence collection kit of claim 1, wherein said evidence collection tape is tamper-proof or tamper-evident.

5. The sexual assault evidence collection kit of claim 1, wherein said instructions on how to collect each type of evidence comprise a recommended order in which said each type of evidence should be collected.

6. The sexual assault evidence collection kit of claim 1, wherein said instructions on how to collect each type of evidence comprise instructions on how to collect one or more of semen, sweat, blood, saliva, hairs, fibers, skin cells, dried secretions, fingerprints.

* * * * *